United States Patent
Whitcombe et al.

(10) Patent No.: US 6,270,967 B1
(45) Date of Patent: Aug. 7, 2001

(54) METHOD FOR DETECTING A NUCLEIC ACID BASE SEQUENCE

(75) Inventors: David Mark Whitcombe; Jannine Brownie; Stephen Little, all of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/171,982
(22) PCT Filed: Apr. 29, 1997
(86) PCT No.: PCT/GB97/01163
§ 371 Date: Oct. 29, 1998
§ 102(e) Date: Oct. 29, 1998
(87) PCT Pub. No.: WO97/42345
PCT Pub. Date: Nov. 13, 1997

(30) Foreign Application Priority Data

May 4, 1996 (GB) .................................................. 9609441

(51) Int. Cl.⁷ .......................... C07H 21/04; C07H 21/00; C07H 19/04; C12P 19/34
(52) U.S. Cl. ........................... 435/6; 435/91.1; 435/91.2; 536/24.3; 536/25.32; 536/26.6
(58) Field of Search ............................. 435/6, 91.2, 91.1; 536/24.3, 25.32

(56) References Cited

FOREIGN PATENT DOCUMENTS

| | | | |
|---|---|---|---|
| 0 332 435 A2 * | 9/1989 | (EP) | ................................. C12Q/1/68 |
| 0 333 465 A2 * | 9/1989 | (EP) | ................................. C12Q/1/68 |
| 0416817 | 3/1991 | (EP) . | |
| 0 639 647 A2 * | 2/1995 | (EP) | ................................. C12Q/1/68 |
| 0678581 | 10/1995 | (EP) . | |
| 0731177 | 9/1996 | (EP) . | |
| 2252407 | 8/1992 | (GB) | ................................. C12Q/1/68 |
| 9325563 | 12/1993 | (WO) | ............................. C07H/15/12 |
| 9421820 | 9/1994 | (WO) | ................................. C12Q/1/68 |
| 95/08642 A1 * | 3/1995 | (WO) | ................................. C12Q/1/68 |

* cited by examiner

Primary Examiner—Kenneth R. Horlick
Assistant Examiner—Joyce Tung
(74) Attorney, Agent, or Firm—Rothwell, Figg, Ernst & Manbeck

(57) ABSTRACT

A method for the detection of diagnostic base sequences in a sample nucleic acid comprises contacting the sample in the presence of appropriate nucleoside triphosphates and an agent for polymerization thereof with a diagnostic primer for the diagnostic base sequence, the primer having a tail sequence comprising a tag region and a detector region such that an extension product of the primer is synthesized when the corresponding base sequence is present in the sample, and any extension product of the diagnostic primer acting as a template for extension of a further primer which hybridizes to a locus at a distance from the diagnostic base sequence. The sample is contacted with a tag primer which selectively hybridizes to the complement of the tag sequence in an extension product of the further primer and is extended, and the presence or absence of the diagnostic base sequence is detected by reference to the detector region in the further primer extension product.

20 Claims, 17 Drawing Sheets detectable fluorophore

METHOD FOR DETECTING A NUCLEIC ACID BASE SEQUENCE

BACKGROUND OF THE INVENTION

1. Field of the Invention

The invention relates to novel methods for the detection of diagnostic base sequences in sample nucleic acid. In particular the invention relates to the use of tailed primers in such methods.

2. Description of Related Art

The invention is an improvement on currently established procedures for the detection of nucleic acid sequences. The detection of nucleic acid sequences is a desirable and necessary procedure in the following exemplary areas; detection and diagnosis of alleles responsible for genetic diseases in humans and other species; detection and diagnosis of DNA sequences associated or linked to genes that may or may not be involved in disease in humans and other species; detection and diagnosis of neoplasms and the effects of therapy of neoplasms; detection of and distinction between different pathogens (eg. viruses, bacteria and fungi); determining the purity of animal strains and pedigrees; distinguishing and identifying different humans and animal samples in forensic medicine.

The polymerase chain reaction (PCR) as disclosed for example in U.S. Pat. Nos. 4,683,202 and 4,683,195 has been used to amplify specific DNA sequences. However, PCR does not, by itself, provide a method to detect single base mutations. It has been necessary to combine the PCR with other techniques, for example allele specific oligonucleotide probing of PCR amplification products.

SUMMARY OF THE INVENTION

We have now devised a novel assay system for the detection of diagnostic base sequences which uses tailed diagnostic primers having a tag region and a detector region. Under appropriate conditions any diagnostic primer extension product acts as a template for extension of a further primer. In which case a sequence complementary to the tag region and the detector region will arise in the further primer extension product. A tag primer is provided which can hybridise to the complement of the tag region in the further primer extension product and be extended. A diagnostic base sequence is identified by reference to the sequence complementary to the detector region in the tag primer extension product.

Therefore in a first aspect of the present invention we provide a method for the detection of a diagnostic base sequence in nucleic acid comprised in a sample, which method comprises contacting the sample under hybridising conditions and in the presence of appropriate nucleoside triphosphates and an agent for polymerisation thereof, with a diagnostic primer for the diagnostic base sequence, the diagnostic primer having a tail sequence comprising a tag region and a detector region, such that an extension product of the diagnostic primer is synthesised when the corresponding diagnostic base sequence is present in the sample, no extension product being synthesised when the corresponding diagnostic base sequence is not present in the sample and any extension product of the diagnostic primer acts as template for extension of a further primer which hybridises to a locus at a distance from the diagnostic base sequence, and contacting the sample with a tag primer which selectively hybridises to the complement of the tag sequence in an extension product of the further primer and is extended, and detecting the presence or absence of the diagnostic base sequence by reference to the detector region in the further primer extension product.

The detector region in the further primer extension product may be detected in a number of ways. For example the sample may be contacted with detector species capable of emitting a detectable signal upon interaction with the detector region in the further primer extension product whereby the presence or absence of the diagnostic base sequence is detected by reference to the detectable signal. It will be appreciated that the detector species cannot become associated with the corresponding detector region until target dependent hybridisation and further primer extension has occurred. This system is well suited for homogeneous assays and real time or end point analysis. A detector species is any species capable of selective association with the detector region in a further primer extension product and release of a detectable signal. It will be appreciated that by "selective association" we mean that the detector species identifies and binds to the detector region in the further primer extension product to the exclusion of other nucleic acid seqences in the sample. Such detector species may include antibodies and hybridisation probe(s). A particular detector species is a detector probe such as a labelled hybridisation probe. Label is conveniently released by the action of for example an exonuclease associated with the polymerase mediated extension of a tag primer. In the specific description hereinafter we describe a number of alternative systems. These include detection of the change in shape of a probe upon hybridisation, the use of two or more probes having interactive labels such as for example the use of fluorescence resonance energy transfer, the use of scintillation proximity assays (SPA), the measurement of a change in fluorescence polarisation upon hybridisation of a fluorescently labelled probe. Further systems will be apparent to the scientist of ordinary skill. These include the use of a solid phase capture probe for the detector region in the further primer extension product. It will be appreciated that both direct and indirect labelling methods may be used to detect the immobilised further primer extension product. By way of example a further labelled probe for a region other than the detector region may be used. Alternatively, intercalation may be used to detect the detector region/probe DNA duplex. Also, labelled dNTPs may be incorporated into the further primer extension product.

The sequence of the detector probe need not be the same but is conveniently identical to the sequence of the detector region in the tail. It will be appreciated that minor changes may be made to the sequence of the detector probe without affecting its performance to any significant extent.

Alternatively the complement of the detector region is detected by reference to its size contribution to the overall amplification product of the tag and further primers. A convenient size difference may be used, even as little as one base pair difference can be detected on a gel. Generally however size differences of at least 5, conveniently at least 10, at least 15 or at least 20 base pairs are used. This aspect of the invention is of particular use where two or more alleles of a genetic locus are to be detected in a single assay mixture.

The tag primer is capable of hybridisation to the complement of the tag sequence in the further primer extension product. It will be understood that the diagnostic primer extension product is separated from the further primer extension product prior to hybridisation of the tag primer. The sequence of the tag primer is conveniently identical to the sequence of the tag region in the tail. The tag primer preferably comprises a sequence capable of hybridisation to all tag sequences. All tag sequences are preferably identical. Again it will be appreciated that minor changes may be made to the sequence of the tag primer without affecting its performance to any significant extent. The use of a common tag primer and common tail sequences has significant cost advantages for a typical assay.

It will be understood that the diagnostic primer tail is non-complementary to any relevant genomic sequence or adjacent region so as not to compromise the assay.

In known diagnostic PCR procedures mispriming may occur at each amplification cycle, especially where the primer is used to detect for example single base mismatches or to detect a particular sequence against a background of related sequences. Such mispriming may only occur as a very low percentage of total priming events per amplification cycle but will increase significantly as a function of the overall number of cycles. The present invention comprises a two stage procedure wherein as a first stage the initial interaction between a diagnostic primer comprising tag and detector regions and a sample template may conducted at optimum hybridisation stringency. Any primer extension products are then amplified using a further primer. As a second stage the above extension products are then amplified using a tag primer and the further primer. Accordingly, whilst mispriming may still initially occur the overall level may be significantly reduced.

As indicated above the tail sequences may be the same or different but are conveniently identical or substantially similar so that a single tail primer may be used. This facilitates the performance of large multiplexes without overloading the reaction mix with different primers. We have found that the use of identical tag sequences can be advantageously used to even out the efficiencies of different amplification reactions.

We have also found that tailed primers can also be used to prevent the formation of "primer dimers" and other inter-primer artefacts. These are a particular problem in homogeneous assays using for example intercalating dyes to detect double stranded nucleic acid. They result in false positive signals. See for example Ishiguro et al, Anal. Biochem., 1995, 229, 207–213, especially pages 211–212. Whilst we do not wish to be limited by theoretical considerations, it is believed that the formation of primer dimers is dependent on some degree of homology between primers and their use at high concentrations. It may be possible to reduce the formation of primer dimers by careful primer design. However where many primers are used at high concentrations, for example in PCR multiplexes, this becomes more difficult. We now disclose the use of diagnostic and further primers which are genome specific at their 3'-termini but which carry a detector region and common extensions (tags) at their 5'-termini. These are used in combination with a common tag primer which can prime from the complement of the tag sequence in extension products of further primer(s). Thus whilst primer dimers and other inter-primer artefacts could occur during first phase diagnostic priming, these cannot be amplified during subsequent rounds of tag specific priming. It will be appreciated that the diagnostic primers are conveniently used at concentrations which allow satisfactory priming on their genomic template(s) but do not allow significant PCR amplification.

The common tag primer is used at higher concentration than the genome specific primers.

To ensure that primer-dimers and other artefacts are avoided a common tag and common tag primer are preferably used for all primers present in a reaction mix, including control primers.

We have now found that it is advantageous to switch from diagnostic primer priming to tag primer priming by means of a temperature switch. The primers are selected so that the melting temperature of the tag primer is higher than the genome complementary region of the diagnostic primer. An increase in temperature will favour priming, for example after one or conveniently two rounds of diagnostic primer priming, by the tag primer.

The diagnostic primer may be an allele specific primer. In EP-A-0333465 (Baylor College of Medicine) there is described a detection method using two competing primers for the detection of diagnostic base sequences which differ by as little as a single base. This method depends on careful control of melting temperature (Tm) and is known as competitive oligonucleotide priming (COP). Competing primers may be used in the method of this invention, either the primers are differentially labelled or the amplification products are separated according to size, for example by the use of different size tails on the primers.

Furthermore in our European Patent, Publication No. 0332435, the contents of which are incorporated herein by reference, we disclose and claim a method for the selective amplification of template sequences which differ by as little as one base. The above method is now commonly referred to as the Amplification Refractory Mutation System (ARMS). This is of particular use, for example, where diagnostic base sequencers) are only present it low concentration in complex nucleic acid mixtures.

Therefore in a preferred aspect of the above detection method a terminal nucleotide of at least one diagnostic primer is either complementary to a suspected variant nucleotide or to the corresponding normal nucleotide, such that an extension product of a diagnostic primer is synthesised when the terminal nucleotide of the diagnostic primer is complementary to the corresponding nucleotide in the diagnostic base sequence, no extension product being synthesised when the terminal nucleotide of the diagnostic primer is not complementary to the corresponding nucleotide in the diagnostic base sequence.

The diagnostic primers for use in the preceding aspect are conveniently designed with reference to our above mentioned European Patent, Publication No. 0332435.

By "substantially complementary" we mean that primer sequence need not reflect the exact sequence of the template provided that under hybridising conditions the primers are capable of fulfilling their stated purpose. This applies equally to diagnostic and tail primers. In general, mismatched bases are introduced into the primer sequence to provide altered extension rates with DNA polymerases. Commonly, however, the primers have exact complementarity except in so far as non-complementary nucleotides may be present at a predetermined primer terminus as hereinbefore described.

In the diagnosis of, for example, cancer the situation may arise whereby it is desirable to identify a small population of variant cells in a background of normal cells. The ARMS system is well suited for this purpose since it discriminates between normal and variant sequences even where the variant sequence comprises a very small fraction of the total DNA. Whilst we do not wish to be limited by theoretical considerations we have successfully performed ARMS assays in which the ratio of mutant to normal DNA was 1:100 and we believe that even larger ratios may be readily used. To optimise the sensitivity of the ARMS reaction it may be performed in isolation ie. with a single ARMS primer since in duplex or multiplex reactions there may be competitive interaction between the individual reactions resulting in a loss of sensitivity. A control reaction is desirable to ensure that a polymerase chain reaction has taken place. In a test for an inherited mutation the copy number of the mutation and other genomic is typically 1:1 or 1:2, so a genomic control reaction can be used without compromising sensitivity or creating an imbalance in the system. In a cancer test however, the use of a genomic control reaction may swamp the test reaction leading to a loss of sensitivity. We have now found that ARMS primer(s) comprising tail sequences may advantageously be used in a two stage amplification procedure comprising a genomic control reaction. In the first stage ARMS primer(s) comprising non-complementary tail(s) are used to amplify any variant sequence which may be present. In addition to the ARMS reaction a genomic control reaction is performed in the same reaction vessel using primers at very low concentration. The control reaction primers also have non-homologous tails which may or may not have the same sequence as the ARMS primer tail(s). In the second stage tail specific primers are added and the temperature increased to prevent the original genomic control primers from functioning. In this second stage any variant sequence product is further amplified and the product of the control reaction from the first stage is also amplified to give a detectable product. Thus the ARMS reaction will only take place if variant sequence is present in the original sample and the control reaction will only function if both the first and second stage amplification reactions have worked.

A further and important use of ARMS is for detecting the presence or absence of more than one suspected variant nucleotide in the same sample. The ability of ARMS to selectively amplify sequences depending on the predetermined nucleotide sequence of the diagnostic primers enables multiple amplification products to be distinguished simply, accurately and with minimal operator skill thus making it possible to provide a robust technique for screening a single sample for multiple nucleotide variations. The use of ARMS to detect more than one suspected variant nucleotide in the same sample is conveniently referred to as multiplex ARMS. Multiplex ARMS is thus of particular interest in screening a single sample of DNA or RNA for a battery of inherited conditions such as genetic disorders, predispositions and somatic mutations leading to various diseases. Such DNA or RNA may for example be extracted from blood or tissue material such as chorionic villi or amniotic cells by a variety of techniques such as those described by Maniatis et al, Molecular Cloning (1982), 280–281. Morever as the molecular basis for further inherited conditions becomes known these further conditions may simply be included in the screening technique of the present invention.

Multiple amplification products may be distinguished by a variety of techniques. Thus for example probes may be employed for each suspected amplified product, each probe carrying a different and distinguishable signal or residue capable of producing a signal.

A much simpler and preferred method of distinguishing between ARMS amplification products comprises selecting the nucleotide sequences of the amplification primers such that the length of each amplified product formed during the process of the present invention is different. In this regard the number of base pairs present in an amplification product is dictated by the distance apart of the diagnostic and amplification primers. Thus the amplification primers may be designed such that each potential variant nucleotide is associated with a potential amplification product of different length.

In an ARMS reaction diagnostic for a particular point mutation the sequence of the primers is largely constrained by the sequence of the DNA adjacent the mutation of interest. The 3' base of the primer usually matches the base altered by the mutation and extra destabilisation is introduced to give the required level of specificity. The term "specificity"refers to the ratio of the yield of product when an ARMS primer is used to prime its target sequence compared to the yield of mis-primed product from the non-target sequence.

In a multiplex ARMS reaction it is desirable that the individual ARMS reactions work with similar efficiency to allow the simultaneous detection of all the reaction products. This may be achieved for example by altering the concentration of the primers, alteration of the number/composition of reactions, or alteration of the ammount of additional destabilisations introduced into the ARMS primers. Whilst these methods are normally sufficient to obtain a balanced multiplex ARMS reaction the use of tail or tag sequences may have advantages in certain situations. In particular these may allow a more specific test. By way of example, where a strong additional mismatch is used to obtain specificity the yield of corresponding multiplex product may be low. Reducing the additional mis-match strength may not be possible without compromising specificity. A tail sequence which in combination with a tail specific primer provides a good substrate for a DNA polymerase may be used to balance the multiplex reaction. A range of tail/primer combinations of known priming ability may be provided. Thus by way of example as a first amplification step the priming/mis-priming ratio is optimised without regard to product yield. Product yield is then balanced in the second amplification step using an appropriate range of tail/primer combinations.

In our UK Patent No. 2252407 (Zeneca) we disclose and claim that multiplex ARMS may be successfully performed where diagnostic primer extension products of more than one diagnostic base sequence of a nucleic acid sample comprise a complementary overlap. This unexpected improvement to multiplex ARMS is referred to hereinafter as overARMS. OverARMS now facilitates the detection and analysis of, for example, inherited or infectious disease where the potential variant nucleotides are closely spaced.

In an overARMS reaction the size of the reaction products can be used to identify individual combinations of variant nucleotides. Where the products are separated for example on an agarose gel this approach may be limited by the resolving power of the gel. By way of example in a high resolution agarose gel overARMS may presently be used to identify mutations within about 10–15 bases of each other. The size of the outer overARMS primer was increased to give a larger product and we surprisingly found that the yield of the smaller overARMS product was significantly reduced. Whilst we do not wish to be limited by theoretical considerations we believe that target masking takes place due to the increased Tm of the larger overARMS primer which binds preferentially to the target DNA and prevents the smaller overARMS primer from hybridising. Use of a tailed outer overARMS primer may provide the increased product size necessary for resolution but since it is non-complementary at its 5' end the Tm will be similar to the smaller primer.

OverARMS is conveniently used for HLA typing, in the diagnosis of β-thalasaemia, sickle cell anaemia, phenylketonuria (PKU), Factor VIII and IX blood disorders and α-1-antitrypsin deficieny. A particular use for OverARMS is in the detection and diagnosis of cystic fibrosis. Convenient cystic fibrosis alleles are disclosed in our European Patent Application No. 90309420.9; by B. Kerem et al, Science, 1989, 245, 1073–1080; by J. R. Riordan et al, Science, 1989, 245, 1066–1073; by J. M. Rommens et al, Science, 1989, 245, 1059–1065; by G. R. Cutting et al, Nature, 346, 366–368; by M. Dean et al, Cell, 61, 863–870; by K. Kobayashi et al, Am. J. Hum. Genet., 1990, 47, 611–615; by B. Kerem et al, Proc. Natl. Acad. Sci. USA, 1990, 87, 8447; by M. Vidaud et al, Human Genetics, 1990, 85, (4), 446–449; and by M. B. White et al, Nature, 344, 665–667.

Our two stage amplification process using diagnostic and tag primers in combination with a further common primer is conveniently carried out using all three primers simultaneously and preferably using a ratio of tail specific and/or further primer(s) to diagnostic primer(s) of at least 1:1, such as at least 20:1, at least 30:1, and at least 40:1, preferably at least 50:1.

All of the above detection methods involving PCR amplification may be provided as homogeneous assays.

The nucleic acid in the sample may be nucleic acid derived from for example viruses, bacteria (genomes and plasmids), bacteriophages, eukaryotic cells (nuclear, plasmid or organelle), humans, animals, plants, latent viruses in human or other cells. The sample is conveniently obtained from an individual using conventional techniques. The nucleic acid may be DNA, RNA or reverse transcribed RNA. It may be native, fragmented, cloned, degraded, extracted from cells or just released upon cell death.

An additional benefit of the method of the invention is in single tube genotyping ARMS assays. At a poylymorphic locus in a diploid organism there are typically two different alleles (A and B) and hence three possible genotypes (AA, AB and BB). One way to determine the genotype is to perform two separate ARMS reactions, one specific for allele A and the other specific for allele B. It is also possible to include both the A- and B-specific ARMS primers in a single reaction and use differential labelling or primer length to determine which of the primers have amplified. In practice there may be problems such as non-specificity since the ARMS reaction product from one allele-specific primer may act as a target for mispriming for the other primer. However in the method of the present invention the initial extension reaction is from the tailed ARMS primer but subsequent amplification is via the tag primer. After, for example the second round of PCR the ARMS primer contributes very little to the amplification process and consequently the probability of inappropriate priming from non-target reaction products is greatly reduced. The use of a temperature shift protocol after say two rounds of PCR to promote tag priming, will further reduce the chance of mis-priming. Detection of the products of different diagnostic primers is by differential product size or differential labelling.

The method of the invention may be used in combination with a number of known detection systems. By way of example it may be used to improve the taqman assay as described for example by Holland et al, Proc.Natl. Acad. Sci.USA, 1991, 88, 7276–7280 and by Gelfand et al in U.S. Pat. No. 5,210,015. A further assay is that described by Yamagata et al in EP-A-0 639647. A still further assay is the strand displacement assay (SDA), see for example Walker et al, Nucleic Acids Research, 1996, 24(2), 348–353, EP-A-0 678 581, EP-A-0 678 582, and EP-A-0 684 315.

The invention will now be further illustrated but not limited by reference to the following detailed description, Example, Table and Figures wherein:

DESCRIPTION OF THE DRAWINGS

Each of FIGS. 1,2,3, and 4 shows the effect of magnesium concentration on the fluorescence ratio of FAM/TAMRA in the TagMan embodiment of the invention.

FIG. 9(*b*) shows complementary strand synthesis from the further primer (cba). A copy of the tailed 3* primer has now been made.

FIG. 10(*a*) shows the further primer extension product (cba and arrow and following dotted line). The tag primer (abc) and probe (xyz) with attached fluorophore and quencher are shown and can now anneal to the copied tail FIG. 10(*b*) shows polymerase mediated extension of the taq primer, this encounters the hybridised probe and efficiently cleaves the probe, releasing the measured fluorophore away from its quencher. This is the same as conventional TaqMan.

FIG. 10(*c*) shows continued amplification of the target region driven by the tag primer (abc) and efficient cleavage of the TaqMan probe (xyz). This allows real time or end point detection of the released fluorophore. The tag primer and the TaqMan probe are included in the PCR at high concentrations, while the long tailed primers are included at low concentrations, to maximise tag driven priming. In order to maximise the efficiency of the process, the TaqMan probe should anneal more strongly than the tag primer, otherwise cleavage will be inefficient. This can be achieved by manipulating the melting temperatures of the primers and their relative concentrations. When using TaqMan for allele discrimination the ASO element of the approach requires that the probe annealing is borderline to obtain maximum differentiation between the two variants. The new system is more easily optimisable because of the probe and drive elements are user-selected and can be optimised once for all amplicons.

FIG. 11 shows the Molecular Beacons embodiment of the invention. Molecular beacons makes use of a similar quenching effect: at the ends of a probe are 5 bp sequences complementary to each other. At each end of the probe is a member of a pair of fluorophores, one absorbs the excitation light and emits it a wavelength which is quenched by the other fluorophore. At low temperatures, the complementary regions of the of the probe cause the formation of the stem loop structure, bringing the two fluorophores close to each other and amplified target, then it should hybridise, disrupting the hairpin and releasing the first fluorophore from the quenching effect of the second.

The Molecular Beacons method is a good way to detect amplicons but not so well suited for allele discrimination. In our new scheme, allele discrimination can be obtained via ARMS but more importantly, the probe region may be designed with the idea of maximising the stretching out effect caused by the hybridisation. In particular, the last 5 bp on the ends of the probe can be made to hybridise to the target rather than "flapping around"; this should allow the use of shorter probes and yield stronger signals. There is no need to design and produce new and expensive probes for each new amplicon, a generic probe can be used for many different amplification targets. The system is multiplexible by changing the probe and introduced target sequences, and using a different pair of matched fluorophores.

Figure 12:
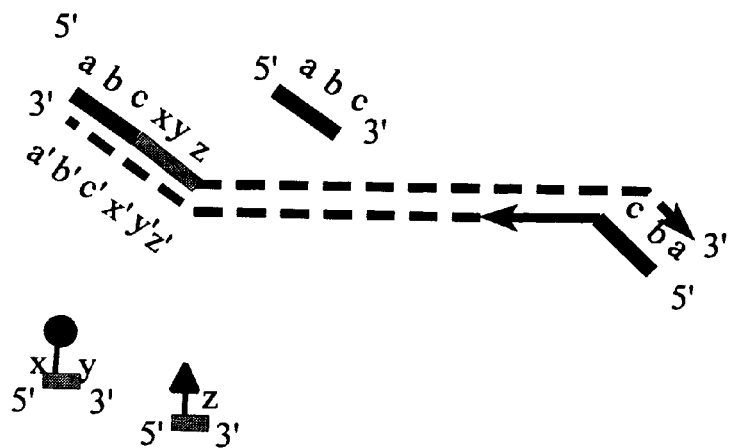
Figure 12B:
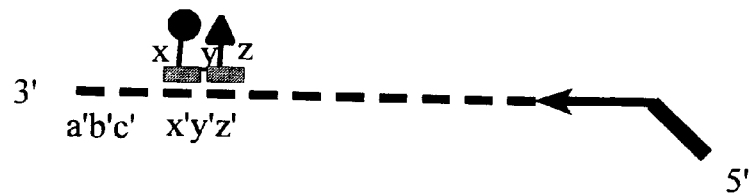

FIG. 12 shows the FRET detection embodiment of the invention. The basic method for this approach is to introduce two probes each carrying a member of a fluorophore pair. When the two probes hybridise to their amplified targets (which are essentially adjacent to each other), the absorbed energy from exciting the first fluorophore is transferred to the second fluorophore which then emits at its characteristic wavelength. This can be greatly shifted from the excitation and emission wavelengths of the first fluorophore and produces very low backgrounds. In this format, the spacing between the two probes is crucial and requires case-by-case optimisation. Furthermore, the use of two fluorescent probes for each amplicon is an expensive and cumbersome path.

FIG. 12(a) shows continued amplification of the target region driven by the tag primer (abc) in combination with the further primer (cba). The middle portion of the primer (detector region) is copied repeatedly. Also shown are two probes (x,y; and z) which each carry half of an energy transfer pair.

FIG. 12(a) shows how, after amplification, the two probes hybridise to the copied middle section of the tag primer. This allows energy transfer between the probes thus generating a detectable signal, with low background.

By allowing the user to define the probe sites, a single probe pair can be designed and optimised. This is then suitable for use against any target. This system can be multiplexed by simply changing the middle portion of the original primer and using a different pair of fluorophores on appropriate probes. A refinement of this technique, suitable for real-tine assays, is to use directly abutting probes which, once hybridised to the introduced target can be ligated together, for example using a thermostable ligase, and thus fixed in their fluorescing configuration. The ligated double probe can then be displaced by the (taq) polymerase. The ligated product may be to be modified to prevent (TaqMan) cleavage of the newly adjoined sequences.

FIG. 13 shows the Capture and Detection embodiment of the invention. The introduced middle section which becomes copied can be used as the sequence by which specific PCR products are captured. Post capture, a detector molecule can be introduced by way of a second target related probe and detection proceeds as appropriate. In this way, mutant and normal amplicons can be decoded, simply by having unique capture sequence.

Figure 13A:
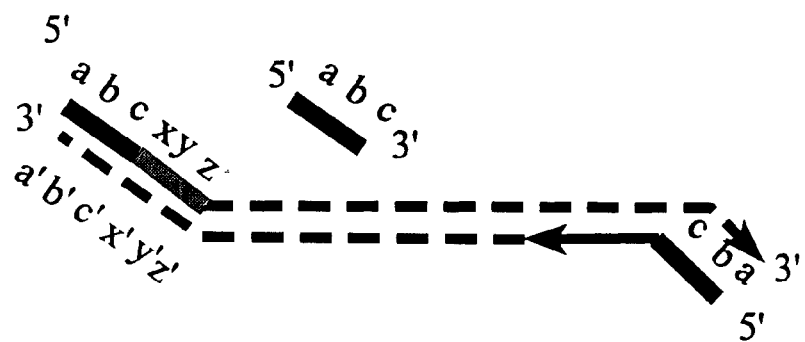

FIG. 13(a) shows continued amplification of the target region driven by the tag primer (abc) in combination with the further primer (cba). The middle section of the further primer extension product is copied repeatedly. Each amplicon may have a characteristic capture signature (ie. xyz can differ).

Figure 13B:
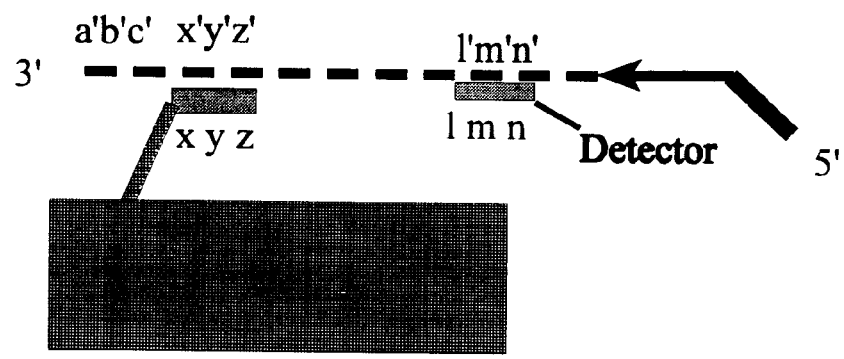

FIG. 13(b) shows how the middle portion (x'y'z') of the further primer extension product is a target for capture by an immobilised probe (xyz). A further probe (lmn) which carries a label (eg. biotin, horse raddish peroxidase, or alkaline phosphatase) may be hybridised to the amplicon for subsequent detection. In this way mutant and normal sequences may be detected in a single vessel, such as a tube, by using different capture regions to discriminate between the two products.

Figure 14A:
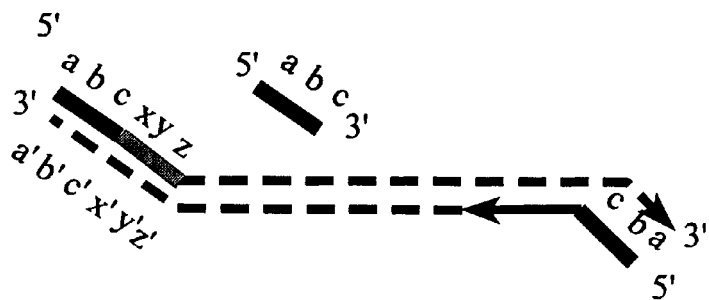
Figure 14A:

FIG. 14 shows the Lanthanide Enhanced Genetics System (LEGS) embodiment of the invention. LEGS is disclosed in our PCT patent application no. WO-95/08642. In LEGS, a partially caged Europium ion is attached to a probe. When a PCR product is rendered single stranded and hybridised to such a probe, a double-stranded region is produced. Also present in the mixture is a synthetic Intercalator/Sensitiser (I/S) molecule which intercalates in the double-stranded region. The intercalator also has a linker arm which ends with a second caging group. In an appropriate conformation, the partially caged Eu ion can become fully caged thanks to the I/S molecule. This excludes and leads to a strong, time-resolved fluorescence effect. The I/S molecule is difficult to synthesise and may not be fully heat stable.

Using the three phase primer of this invention, the middle phase can be constructed to allow a probe carrying a chelate of Eu to hybridise adjacent to a second probe bearing another caging group. This generates a fully caged Eu ion which then fluoresces. A major advantage of this system is that no complex organic synthesis is required. In addition, the second chelator can be introduced in a targeted manner. Using known techniques, both the Eu chelated probe and the cage probe can be readily synthesised.

FIG. 14(a) shows continued amplification of the target region driven by the tag primer (abc) in combination with the further primer (cba). The middle section of the further primer extension product is copied repeatedly. The mixture also contains two probes (x,y: and z), one of which carries a chelated lanthanide, the other carries a second chelating group.

Figure 14B:
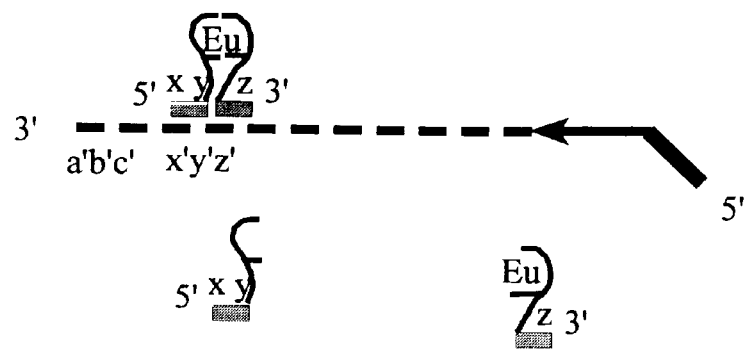

FIG. 14(b) shows how, after amplification, the two probes hybridise to the copied middle section of the further primer extension product. This causes complete caging of the lanthanide ion resulting in high efficiency time resolved fluorescence.

FIG. 15 shows probe cleavage detection methods other than using the 5' exomculease activity of taq polymerase. The probe and the introduced target may differ by one or more bases, rendering any duplex formed between the two susceptible to cleavage by a number of methods, such as chemical cleavage or "cleavase" enzyme. Other approaches include the introduction of a restriction site on the middle position of the primer. After PCR, this may be cleaved releasing the detected fluorophore from its quencher. The newly synthesised DNA may be restriction endonuclease resistant (e.g. by using methylated or phosphothioate dNTPs). We then allow the unprotected probes to be nicked when annealed to the target. Using a thermostable endonuclease would render this assay format fully homogeneous and suitable for real time detection. Alternatively, some enzymes require methylated double-stranded DNA for cleavage and these in combination with a methylated probe provide a further detection system.

Figure 15A:
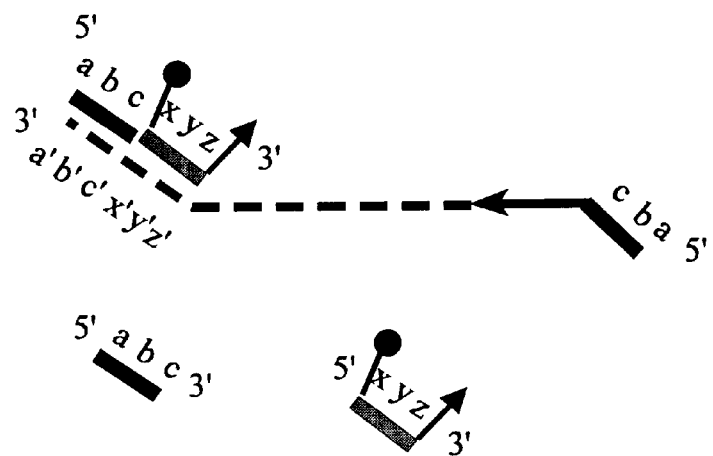

FIG. 15(a) shows shows the further primer extension product (cba and arrow and following dotted line). The tag primer (abc) and probe (xyz) with attached fluorophore and quencher are shown. These may anneal to the copied tail.

Figure 15B:
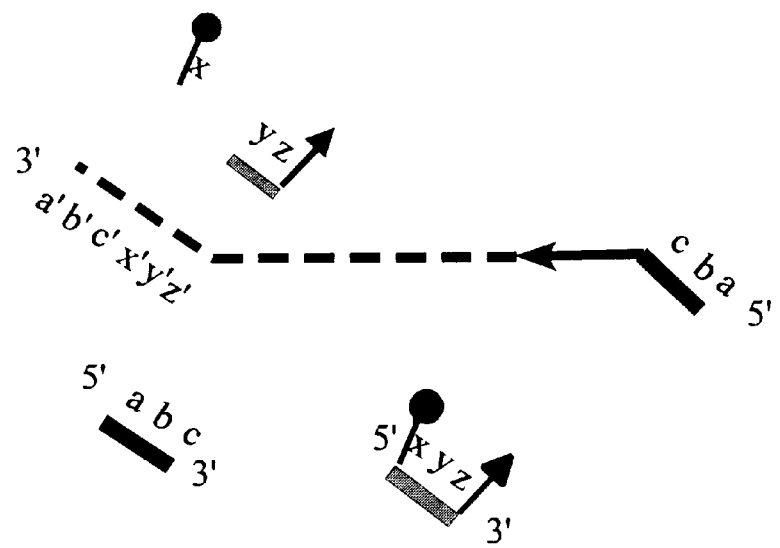

FIG. 15(b) shows the probe (xyz) being cleaved using chemical or enyzmatic methods.

FIG. 16 shows other binding based methods. The introduced and copied, middle segment of the primer may also be designed as the target for a number of specific binding techniques, which may be suitable for product detection. For example, a triple helix motif may be introduced allowing specific detection of completed double-stranded amplicons. Another example is mismatched probes detected by mismatch binding proteins. Other sequence specific protein binding events may be suitable for detection of the amplified middle segment. Finally, simple FP probes may be detected and enhanced by having protein binding superimposed upon the probe/target hybridisation.

Figure 16A:
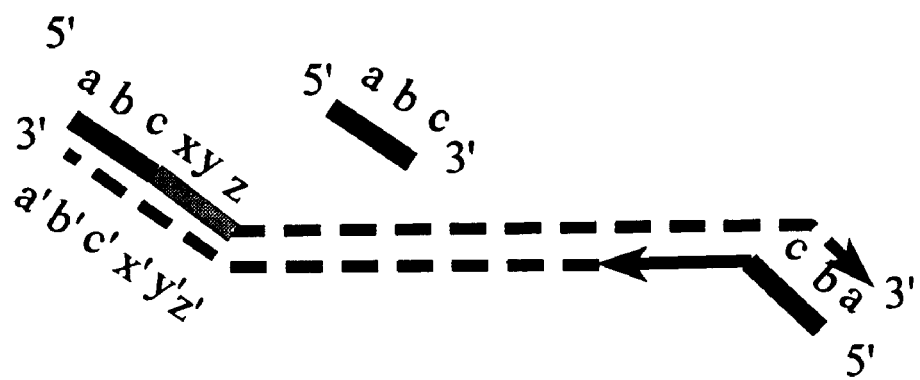

FIG. 16(a) shows continued amplification of the target region driven by the tag primer (abc) in combination with the further primer (cba). The middle section of the further primer extension product is copied repeatedly. Each amplicon may have a characteristic capture signature (ie. xyz can differ).

Figure 16B:
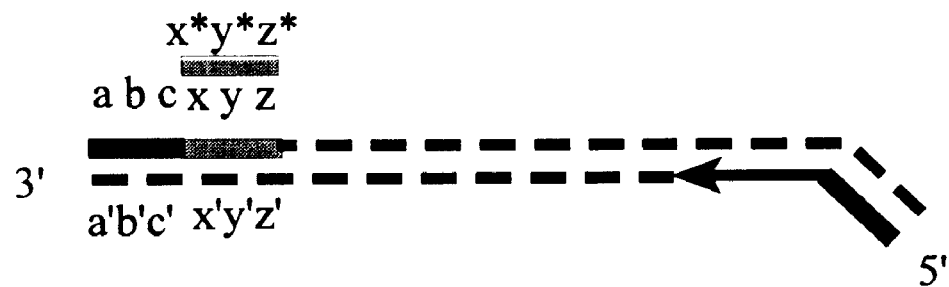

FIG. 16(b) shows how the copy of the middle portion (x'y'z') of the further primer extension product is a target for subsequent binding of a number of detector molecules. A triple helix is formed using probe x*y*z*.

FIG. 17 shows single tube genotyping using differentially labelled 3* ARMS primers.

Figure 17A:
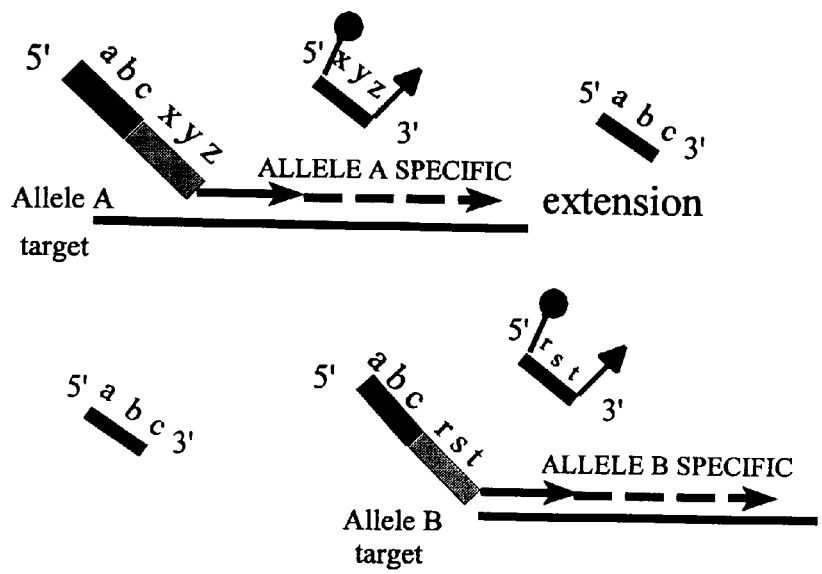

FIG. 17(a) shows allele specific extension of differentially labelled ARMS 3* primers (abcxyz and abcrst) on targets sequences (alleles A and B). Also shown is a common tag primer (abc).

Figure 17B:
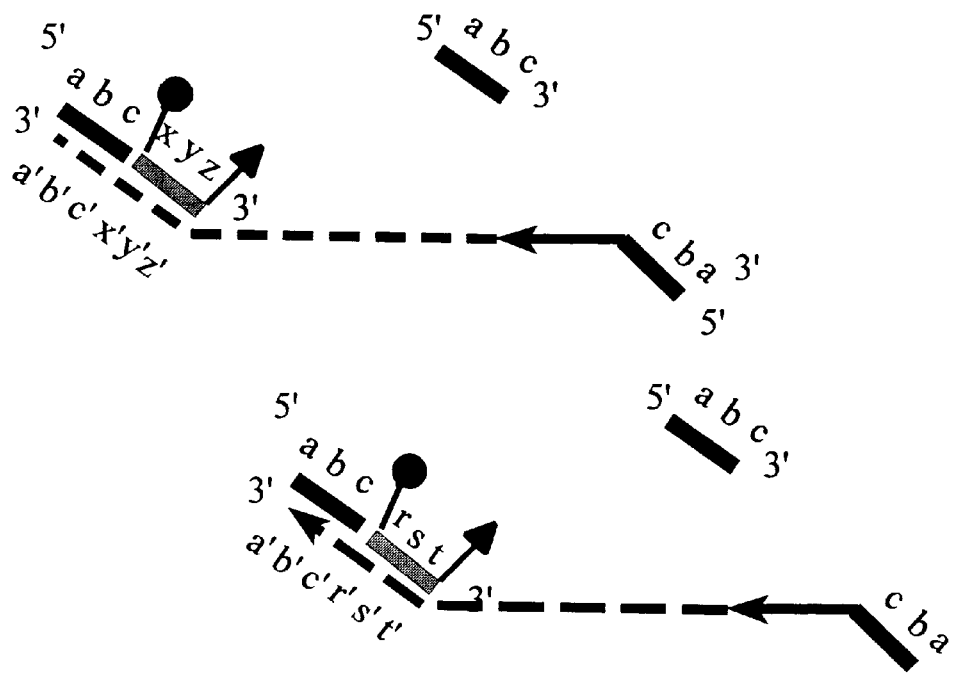

FIG. 17(b) shows that subsequent amplification for both allele A and B specific ARMS products is from the common tag primer (abc). Products from the A specific ARMS primer now contain the reporter sequence xyz, whereas products from the B specific ARMS primer contain the reporter sequence rst. Differential detection is conveniently by size (xyz and rst are of different lengths) or by signal detection (xyz and rst reporter groups produce different signals).

EXAMPLE 1

Materials and Methods
Primers and Probes

| Code | Comment | (5') Amplifier Portion | (Middle) Reporter portion | (3') Genome Priming portion |
| --- | --- | --- | --- | --- |
| S7970 | Amplifies Tagged amplicon | 5'CGTACCACGT GTCGACT3'(SEQ ID NO:14) | NONE | NONE |
| HpH1F | insulin gene | 5'AGCAGGTCTG TTCCAAGG3'(SEQ ID NO:17) | NONE | Primer/amplifier sequence |
| HpH1R | insulin gene | 5'CTTGGGTGTG TAGAAGAAGC3'(SEQ ID NO:18) | NONE | Primer/amplifier sequence |
| INS-BF1 | insulin gene-probe | NONE | 5'FAM-CCTGCCTGTCT CCCAGATCAC TAMRA3'(SEQ ID NO:19) | NONE |
| S7033 | ΔF508 common primer (Amplifier tailed) | 5'CGTACCACGT GTCGACT3'(SEQ ID NO:16) | NONE | 5'CACTAATG AGTGAACAA AATTCTCACC ATT3'(SEQ ID NO:20) |
| T2120 | TagMan Probe | NONE | 5'FAM-CTGGCATCGG TAGGGTAAGG ATCGGTATCGT AMRA3'(SEQ ID NO:21) | NONE |
| T0990 | Triple-phase primer for ΔF508 amplicon | 5'CGTACCACGT GTCGACT3'(SEQ ID NO:16) | 5'(GCGTACT)C TGGCATCGGT AGGGTAAGGA TCGGTATCG3'(SEQ ID NO:22) Bracketed portion is an optional | 5'GCCTGGCA CCATTAAAG AAAATATCA TTGG3'(SEQ ID NO:23) |

-continued

Materials and Methods
Primers and Probes

| Code | Comment | (5') Amplifier Portion | (Middle) Reporter portion | (3') Genome Priming portion |
|------|---------|------------------------|---------------------------|-----------------------------|
| | | | "hinge" region | |
| P1292 | No reporter target primer | 5'(GCGTACT)CG TACCACGTGTC GACT3'(SEQ ID NO:24) Bracketed portion is an optional "hinge" region | NONE | 5'GCCTGGCA CCATTAAAG AAAATATCA TTGG3'(SEQ ID NO:23) |

PCRs
1. Insulin amplicon: 25 µl reactions containing
   3 mM $MgCl_2$
   200 µM dNTPs
   10% (v/v) glycerol
   3 ng/ml each of primers HpH1F and HpH1R
   50 nM INS-B1F probe
   5 µl genomic DNA (or water for negative controls)
   0.625 units of Taq polymerase
   in 1×Amplitaq Buffer
   These reactions were performed using a two step cycle:
   40 cycles×{94° C. for 1 min; 58° C. for 2 min}
2. Ya reactions (150 µl) contained 1×ARMS buffer with: 100 µM dNTPs. Primers
   T0990 and S7033 at 10 nM, S7970 at 500 nM, T2120 at 50 mM, 225 ng ΔF508
   homozygote DNA and 6 unites of Taq Polymerase. Some reactions were
   supplemented with Mg to 2.4 or 4.4 mM
   Yi reactions were identical to Ya, but the target DNA was a normal homozygote at the
   F508 position.
   Other controls contained no target DNA
   To control for the reporter sequence in the Triple phase primer, P1292 (containing no middle portion) was substituted for T0900.
   The PCR cycles were: 2×{94° C. for 1 min}, 62° C. for 2 min, 72° C. for 1 min), followed by 40×{94° C. for 1 min, 64° C. for 1 min}.

Analysis
After cycling, an aliquot (10 µl) of each reaction was analysed by gel electrophoresis to establish the efficiency of amplification.
The remainder was analysed in 100 µl cuvettes using the Fluoromax fluorometer. Where necessary (as in the case of the insulin amplifications), replicate samples were pooled. The excitation wavelength was set to 488 nm and the emission was read at 518 nm (for FAM) and 582 nm (for TAMRA). The ratios were calculated in each case and plotted appropriately.

Figure 1:
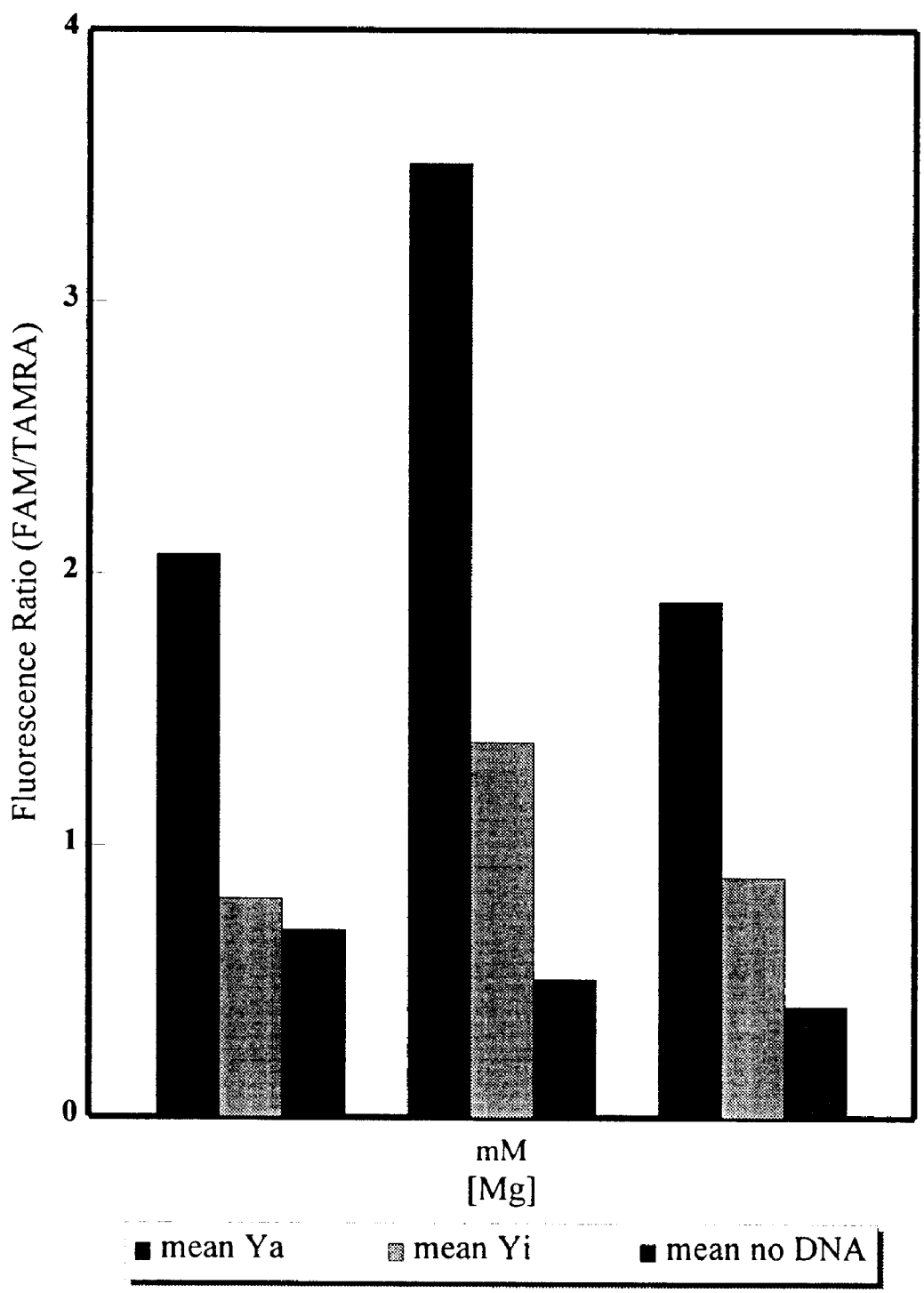
FIG. 1. The difference between Ya and the No DNA samples is strongest at 2.4 mM Mg. However, these conditions also favour ARMS mispriming and the difference between Ya and Yi is smaller; this is an ARMS dependent event.

Results
The optimal [Mg] for the insulin gene region had been established as 3 mM (John Todd pers. comm.) Indeed, there was little or no change in the fluoroesence ratio at lower concentrations. This was borne out in the data shown in FIG. 1. The difference between Ya and the No DNA samples is strongest at 2.4 mM Mg. However, these conditions also favour ARMS mispriming and the difference between Ya and Yi is less impressive: this is due to ARMS not TagMan.

Figure 2:
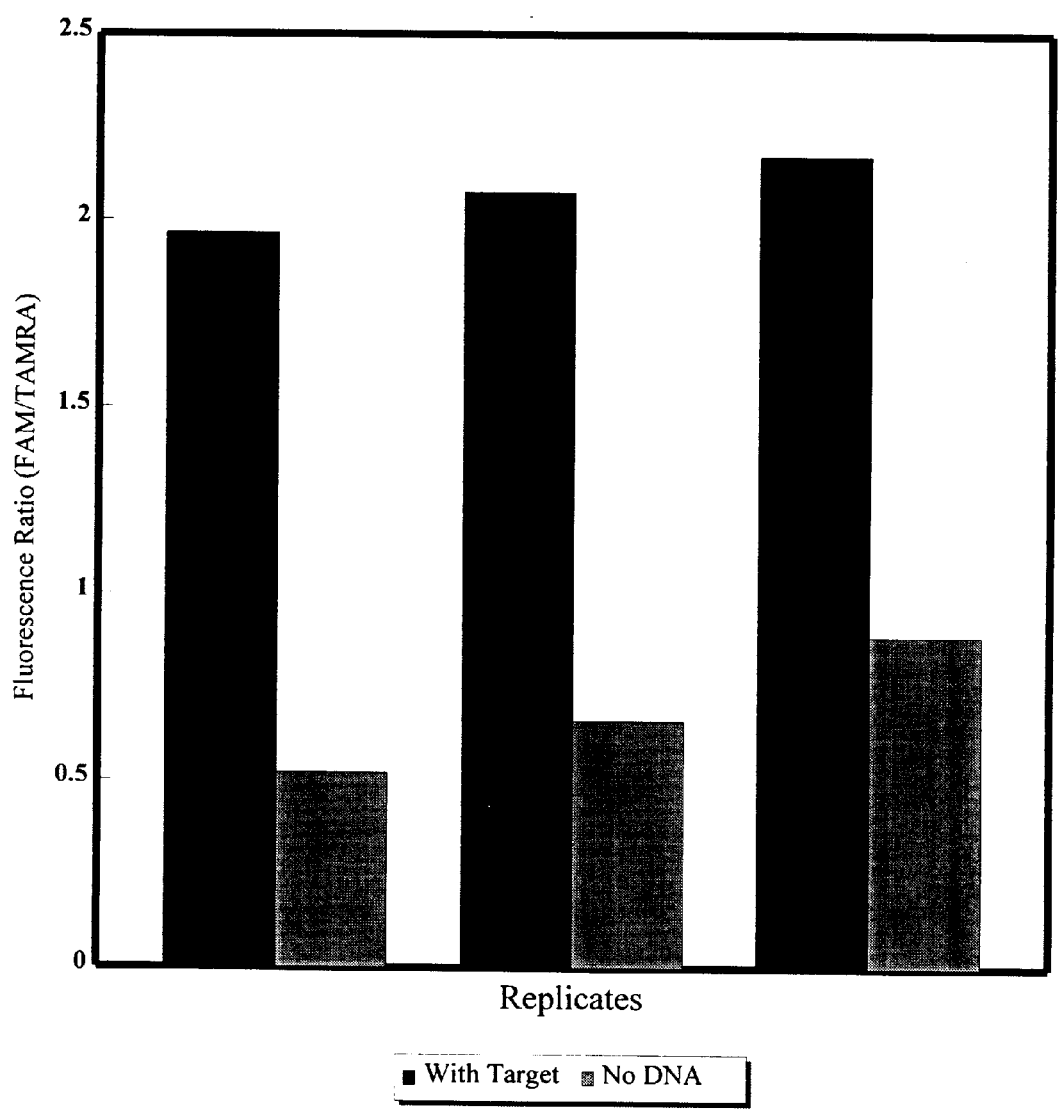
FIGS. 2–4. Each of three replicates for Ya and No DNA is presented for three different Mg concentrations (FIG. 2—1.2 mM Mg, FIG. 3—2.4 mM Mg, FIG. 4—4.4 mM Mg). The reproducibility is good and the ratios between positive and negative samples is impressive.
Figure 3:
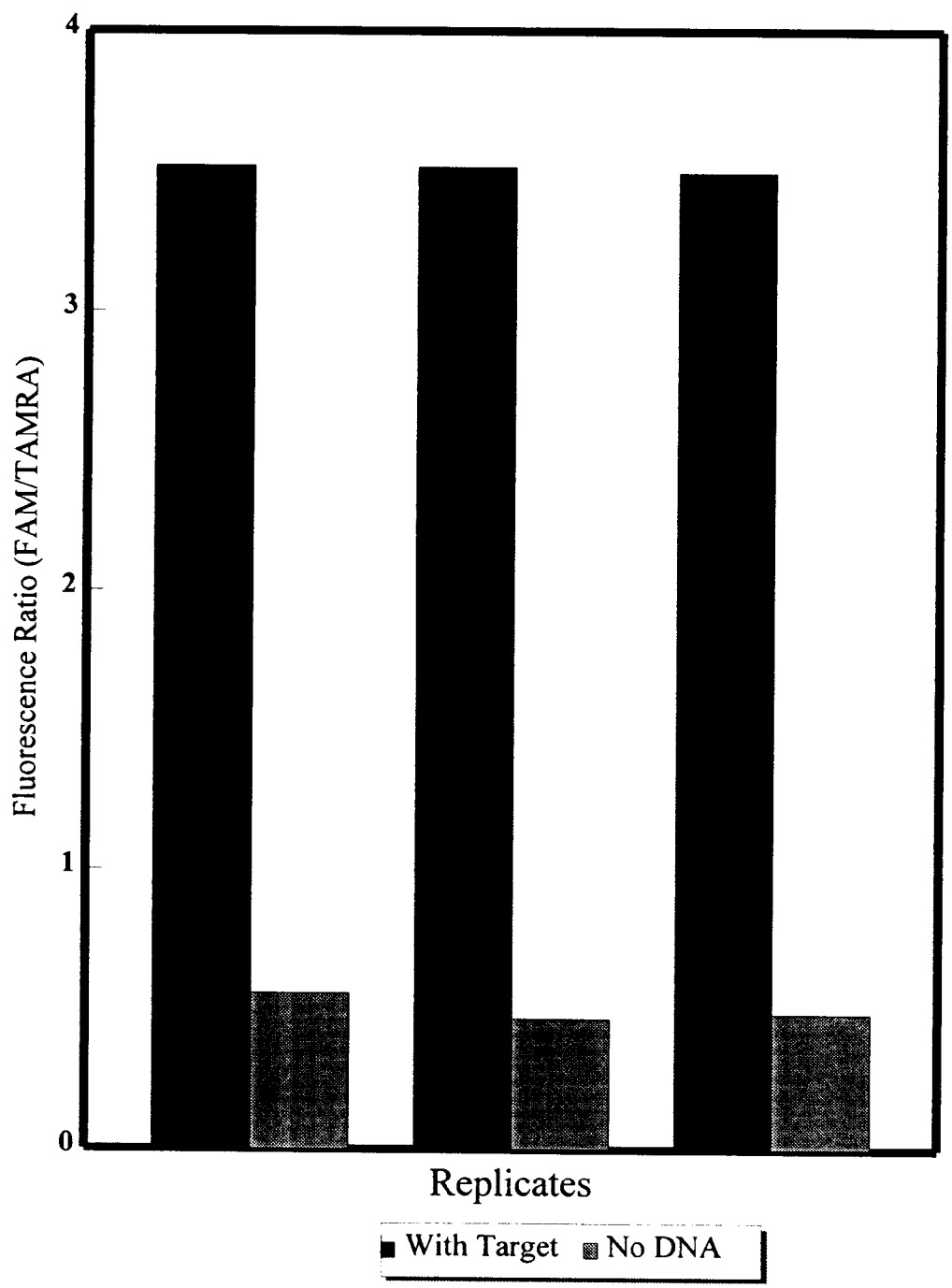
Figure 4:
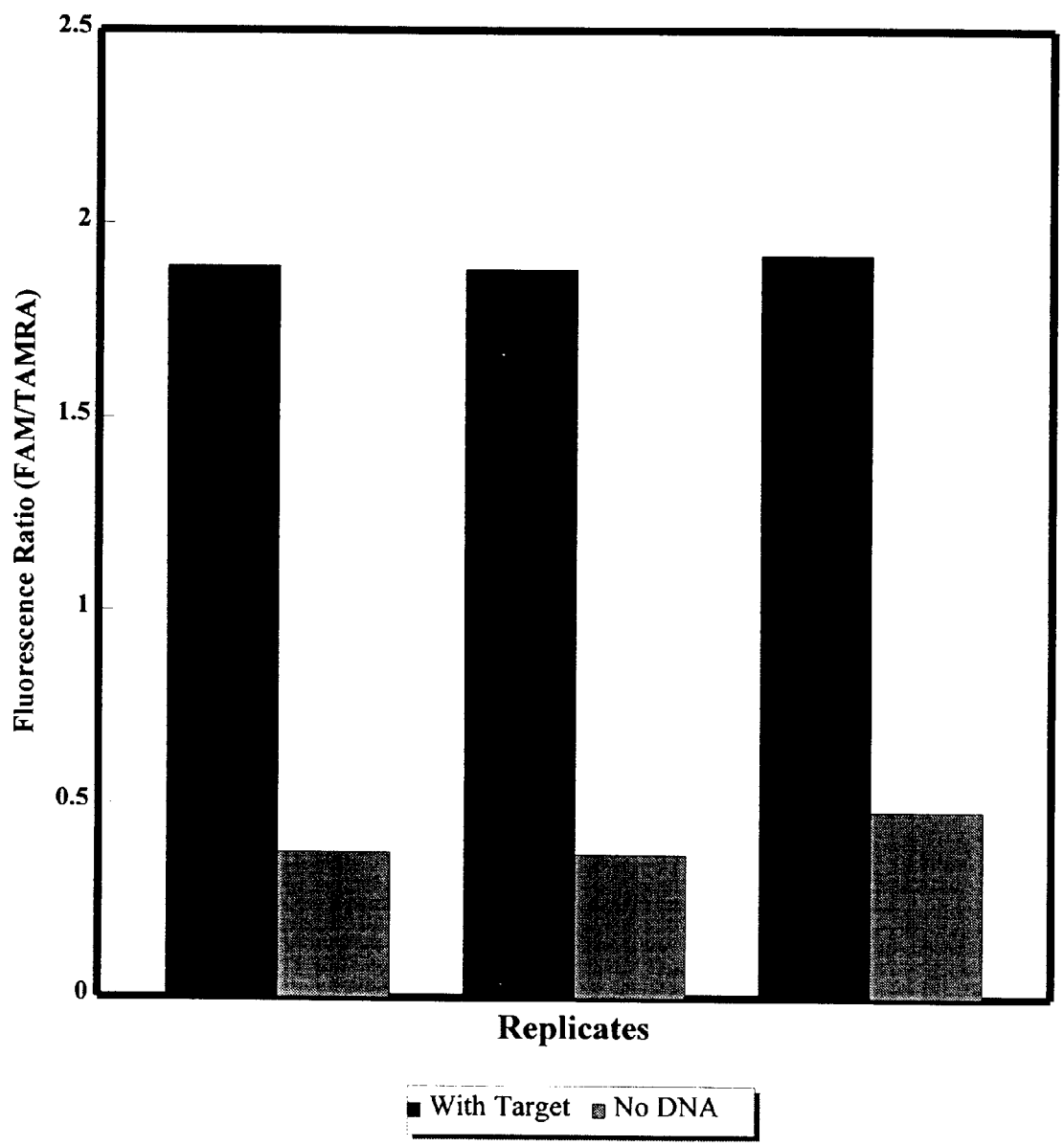

Each of three replicates for Ya and no DNA is presented FIGS. 2–4) for three different Mg concentrations. The reproducibility is good and the ratios between positive and negative samples in impressive.

Figure 5:
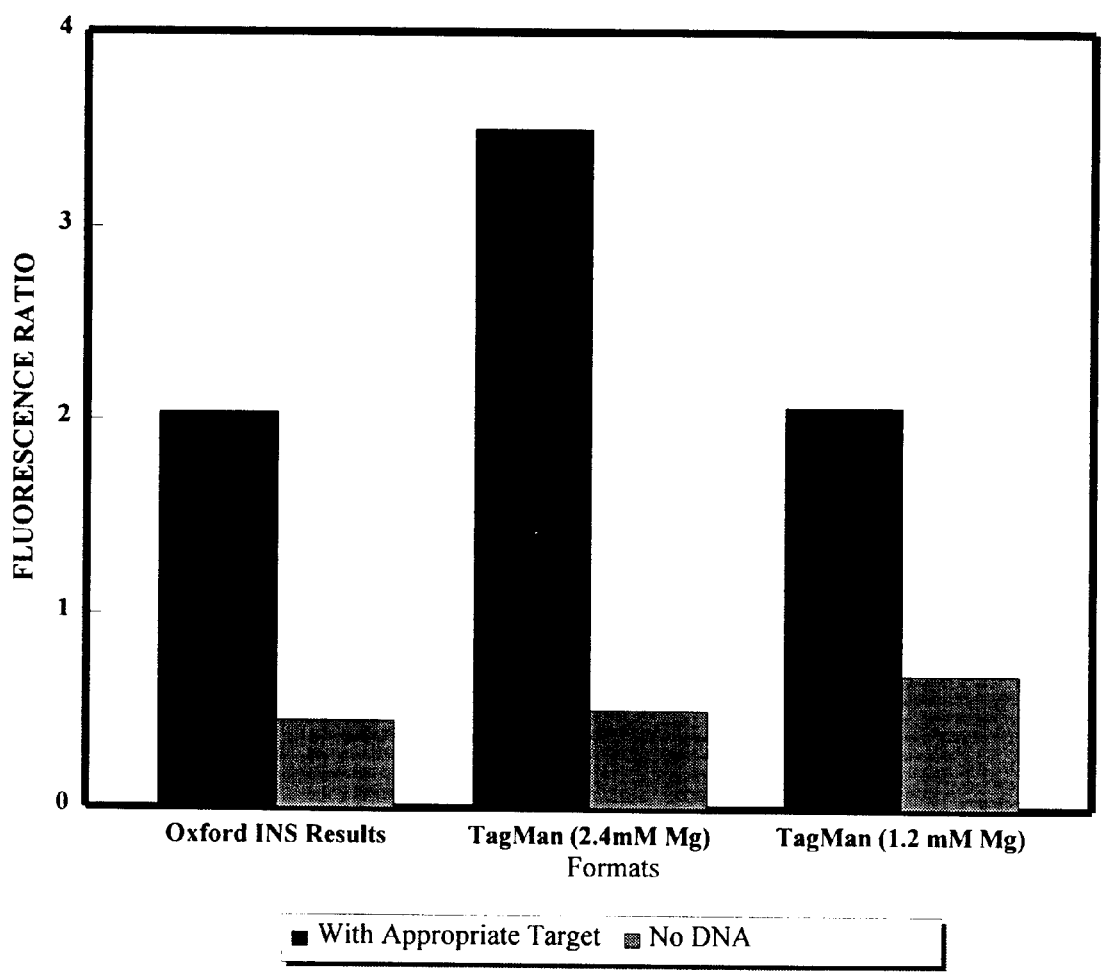
FIG. 5 shows a comparison of a TagMan assay of the invention with an optimised TaqMan assay, looking at an Insulin gene polymorphism). TagMan performed well. Indeed, at 2.4 mM Mg, the difference between positive and negative results was nearly two-fold better than that for the insulin amplicon. We believe that the TagMan probe anneals far more avidly than the amplifying TAG primer.

When compared to the results obtained in an optimised TaqMan assay (the Insulin gene polymorphism) the method of this invention performed well (FIG. 5). Indeed, at 2.4 mM Mg, the difference between positive and negative results was nearly two-fold better than that for the insulin amplicon. This probably reflects the fact that we were able to design the TagMan probe to anneal far more avidly than the amplifying tag primer.

Figure 6:
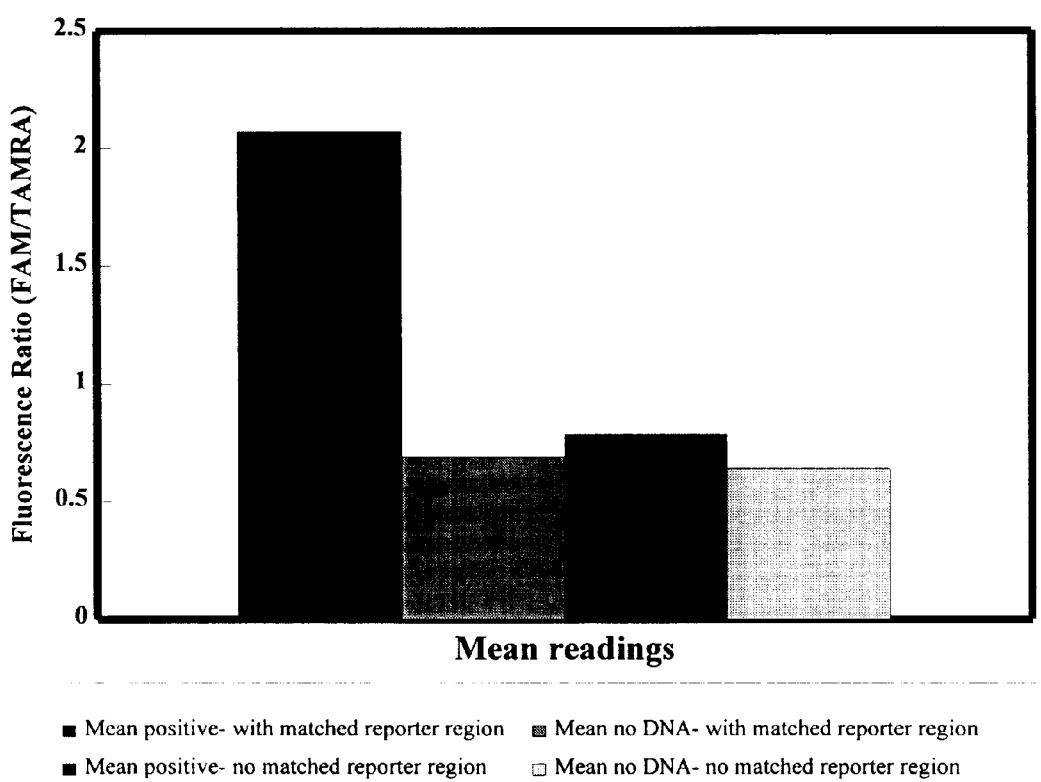
FIGS. 6–8 show comparisons with various controls. In order to be sure that signals obtained were produced as a result of the introduced reporter portion of the original primer, control experiments using tailed primers missing this portion were carried out (FIG. 6—1.2 mM Mg, FIG. 7—2.4 mM Mg, FIG. 8—2.4 mM Mg). In all cases, the absence of the reporter region lead to fluorescence ratios comparable to the negative controls. No inappropriate probe cleavage was taking place under the conditions tested here.
Figure 7:
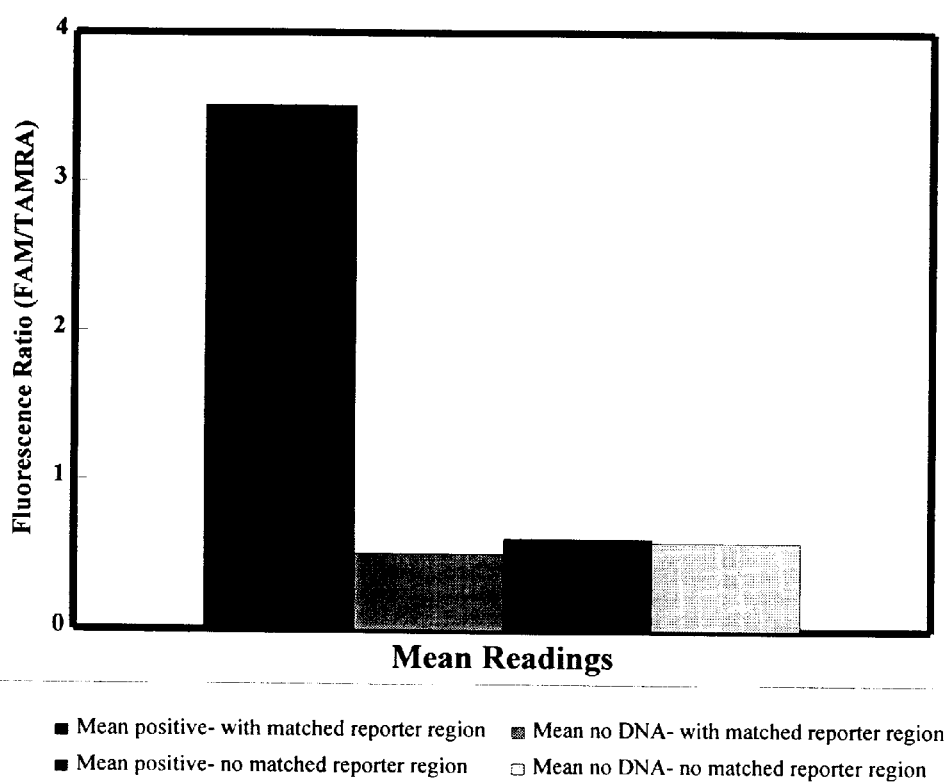
Figure 8:
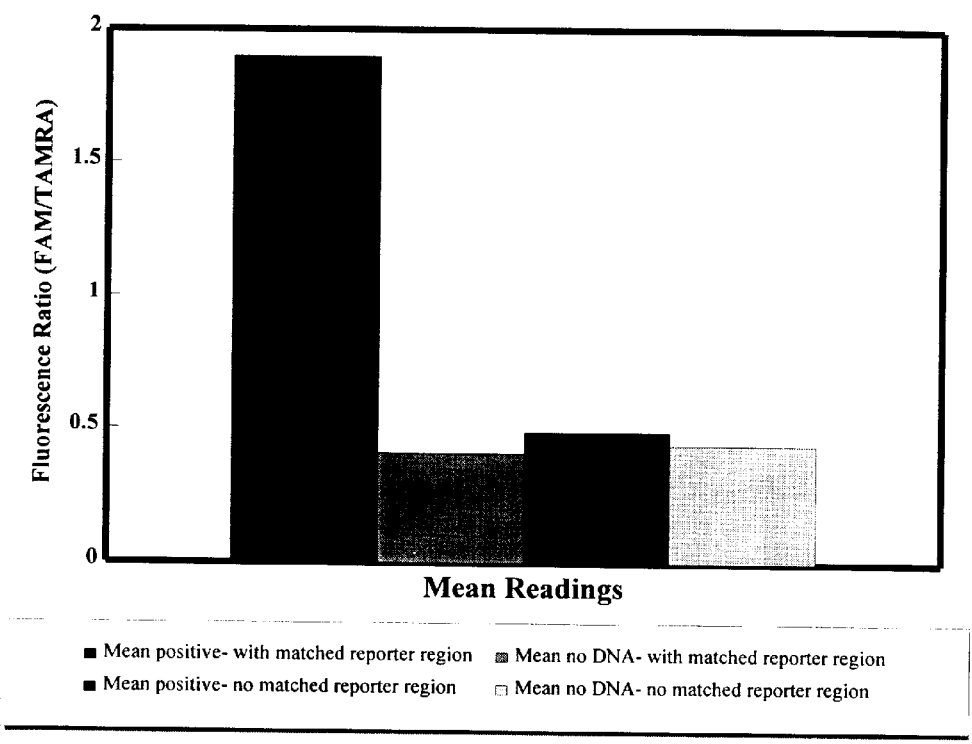
Figure 9A:
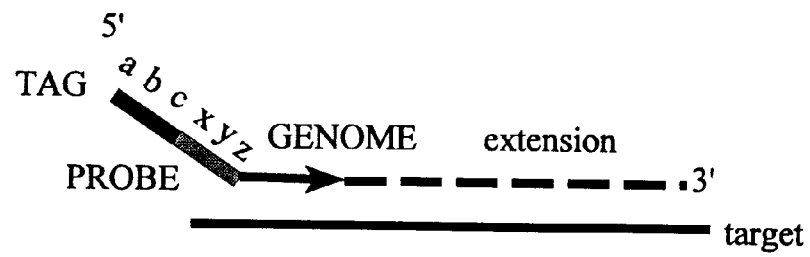
FIG. 9(*a*) shows genomic priming using the tailed three phase (3*) primer of the invention. The tag region of the tail (abc) and the detector region (xyz) are shown as is the tag primer (abc).
Figure 9B:
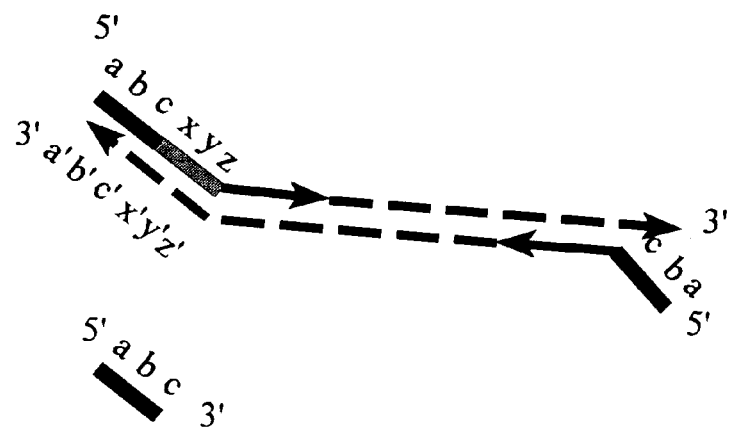
Figure 10A:
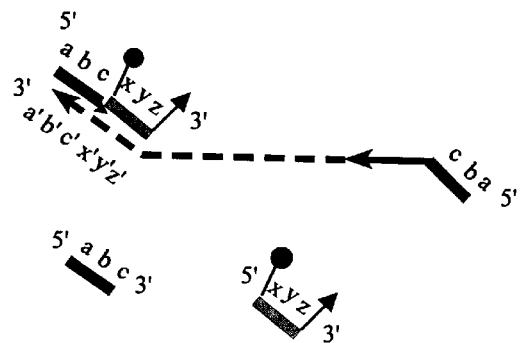
FIG. 10 shows the TagMan detection embodiment of the invention.
Figure 10B:
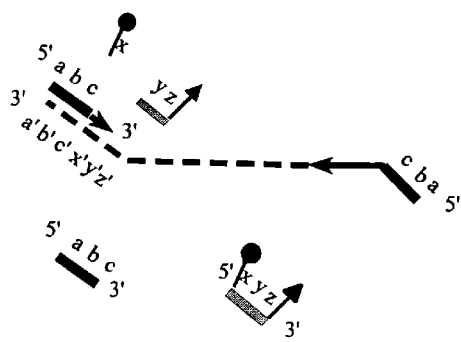
Figure 10C:
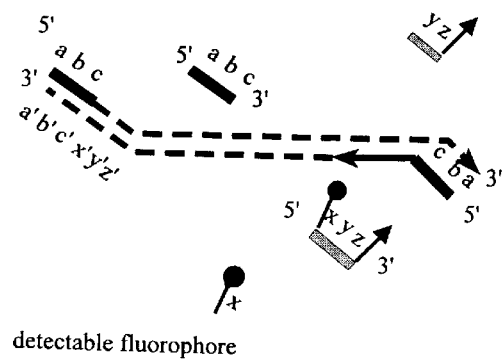
Figure 11A:
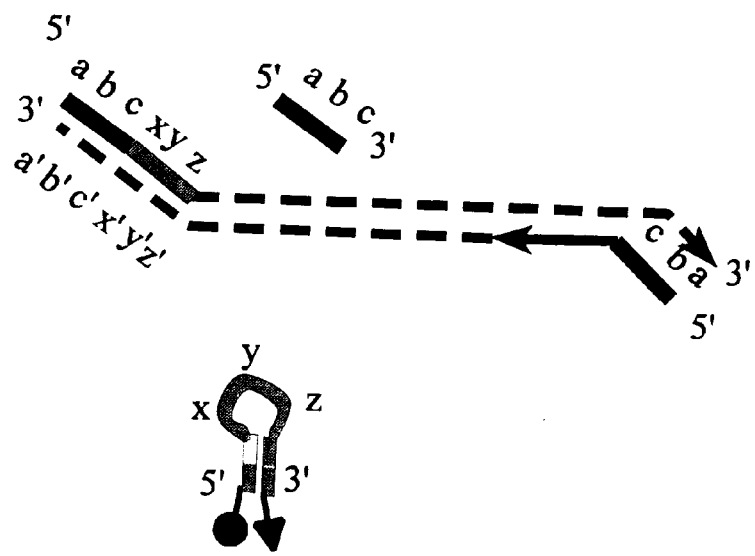
FIG. 11(a) shows the the further primer extension product (cba and arrow and following dotted line). The tag primer (abc) and molecular beacons probe (xyz) can now anneal to the copied tail. Continued amplification of the target region is driven by the tag primer, the middle portion of the primer is copied repeatedly.
Figure 11B:
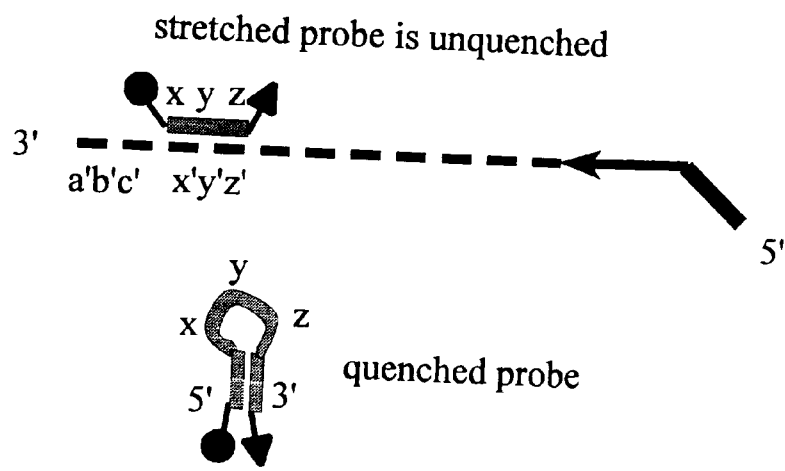
FIG. 11(b) shows a further primer extension product resulting from the continued amplification. The quenched beacons probe (xyz) hybridises to the copied middle section of the tag primer. It becomes stretched, releasing the emitting fluorophore from the quenching effect of the second fluorophore.

In order to be sure that signals obtained were produced as a result of the introduced reporter portion of the original primer, control experiments using tailed primers missing this portion were carried out (FIGS. 6–8). In all cases, the absence of the reporter region lead to fluorescence ratios comparable to the negative controls. No inappropriate probe cleavage was taking place under the conditions tested here. To demonstrate the universality of this approach, a number of further amplicons have been worked up to 3* format In each case, the separate allele specific reactions have been successfully combined to permit Single Tube Genotyping (STG). In one case (factor V Leiden) the assay has been blind tested extensively on clinical samples (which were typed independently by a clinical laboratory using a different technology).

1. Cystic Fibrosis Delta F508
Primers (See Table 1):
   V663 1: Tag 20a
   V6632 common primer, tailed with 20a sequence
   V6634: 3* primer, mutant sequence, T2120 reporter
   V6634: 3* primer, normal sequence, T4029 reporter
Probes:
   T2120: FAMITAMRA labelled,
   T4029: TET/TAMRA labelled,
Reaction Mixes:
   All reactions were in 1×ARMS buffer with $MgCl_2$ adjusted to 3.5 mM final, plus ROX internal standard at 60 nM final, and Tag20a at 500 nM. Amplitaq Gold was included at 2 U per 50 µl reaction
   Three mixes were typically used
   a. Normal only reaction, with primers V6635 and V6632 each at 10 nM, T4029 at 50 nM
   b. Mutant only reaction, with primers V6634 and V6632 each at 10 nM, T2120 at 50 nM
   c. STG with all three primers included at 10 nM, both probes at 50 nM each Cyling Conditions:
  20 minutes at 94° C. to activate the Amplitaq Gold
  2 cycles of 94° C., 40 s; 62° C., 80 s; 72° C. 40 s (genomic priming)
  40 cycles of 94° C, 4 s, 62° C., 80 s (Tag priming)

2. CTLA4A polymorphism
Primers (See Table 1):
  V663 1: Tag20a
  V356 1: Common primer, tailed with Tag 20a sequence
  V6558: 3* primer, mutant specific, carries the TET reporter region (T4029)
  V6715: 3* primer, normal specific, carries the FAM reporter region (T2120)
Probes:
  T2120: FAM/TAMRA labelled,
  T4029: TET/TAMRA labelled,
Reaction Conditions:
  All reactions were in lXARMS buffer with MgCl, adjusted to 3.5 mM final, plus ROX internal standard at 60 nM final, and Tag20a at 500 nM. Amplitaq Gold was included at 2 U per 50 µl reaction
  Three mixes were typically used
  a. Normal only reaction, with primers V6715 and V3561 each at 10 nM, T2120 at 50 nM
  b. Mutant only reaction, with primers V6558 and V3561 each at 10 nM, T 4029 at 50 nM
  c. STG with all three primers included at 10 nM, both probes at 50 nM each
Cycling Conditions:
  20 minutes at 94° C. to activate the Amplitaq Gold
  3 cycles of 94° C., 40 s; 64° C., 80 s; 72° C., 40 s (genomic priming)
  40 cycles of 94° C., 4 s, 64° C., 80 s (Tag priming)

3. BRCA2exon10 polymorphism
Primers (See Table 1):
  V6631: Tag 20a
  R432-96: common primer, tailed with Tag 20 sequence
  V9596: 3* primer, A-variant specific, carries T4029 (TET) reporter sequence
  W1940: 3* primer, C-variant specific, carries T2120 (FAM) reporter sequence
Probes
  T2120: FAM/TAMRA labelled,
  T4029: TET/TAMRA labelled,
Reaction Conditions:
  All reactions were in 1xARMS buffer with MgCl₂ adjusted to 3.5 mM final, plus ROX internal standard at 60 nM final, and Tag20a at 500 nM. Amplitaq Gold was included at 2 U per 50 µl reaction
  Three mixes were typically used
  a. "A" only reaction, with primers R432-96 and V9596 each at 25 nM, T4029 at 50 nM
  b. "G" only reaction, with primers R432-96 and W1940 each at 25 nM, T2120 at 50nM
  c. STG with all three primers included at 25 nM, both probes at 50 nM
Cycling Conditions:
  20 minutes at 94° C. to activate the Amplitaq Gold
  4 cycles of 94° C., 40 s; 60° C., 80 s; 72° C., 40 s (genomic priming)
  45 cycles of 94° C., 40 s, 64° C., 80 s (Tag priming)

4. Factor V Leiden Mutation
Primers (See Table 1):
  V0651: 3* primer (wild type sequence) with reporter region corresponding to T2120
  V0652: 3* primer (mutant sequence) with reporter region corresponding to T4029
  W4085: Tailed common primer
  Tag 20a: Driver primer found in the common and the specific primers
Probes:
  T2120: FAMITAMRA labelled,
  T4029: TET/TAMRA labelled,
Reaction mixes:
  All reactions were in 1xARMS buffer with MgCl₂ adjusted to 3.5 mM final, plus ROX internal standard at 60 nM final, and Tag20a at 500 nM. Amplitaq Gold was included at 2 U per 50 µl reaction
  Three mixes were typically used
  a. Normal only reaction, with primers W4085 and V0651 each at 25 nM, T2120 at 50 nM
  b. Mutant only reaction, with primers W4085 and V0652 each at 25 nM, T4029 at 50 nM
  c. STG with all three primers included at 25 nM, both probes at 50 nM
Cycling Conditions:
  20 minutes at 94° C. to activate the Amplitaq Gold
  3 cycles of 94° C., 41 s; 60° C., 80 s; 72° C., 51 s (genomic priming)
  45 cycles of 94° C., 41 s, 66° C., 80 s (Tag priming)
Validation
  More than 200 clinical samples have been tested blind with the STG mix. In every case, the results obtained were concordant with those obtained by clinical collaborators who used PCR and restriction digestion to type the same samples.

TABLE 1

| CODE  | SEQUENCE | |
|-------|----------|---|
| V6631 | GCGTACTAGCGTACCACGTG | (SEQ ID NO:1) |
| T4029 | CGGTGGACGTGACGGTACGACGAGGCGACG | (SEQ ID NO:2) |
| T2120 | CTGGCATCGGTAGGGTAAGGATCGGTATCG | (SEQ ID NO:3) |
| V6632 | GCGTACTAGCGTACCACGTGCACTAATGAGTGAACAAAATTCTCACCATT | (SEQ ID NO:4) |
| V6635 | GCGTACTAGCGTACCACGTGTCGACTCGGTGGACGTGACGGTACGACGAGGCGACGGCCTGGCACCATTAAAGAAAATATCATCTT | (SEQ ID NO:5) |

TABLE 1-continued

| CODE | SEQUENCE | |
|------|----------|---|
| V6634 | GCGTACTAGCGTACCACGTGTCGACTCTGGCATCGGTAGGGTAAG<br>GATCGGTATCGGCCTGGCACCATTAAAGAAAATATCATTGG | (SEQ ID NO:6) |
| V3561 | GCGTACTAGCGTACCACGTGATCCTGAAACCCAGCTCAAAT | (SEQ ID NO:7) |
| V6558 | GCGTACTAGCGTACCACGTGTCGACTCGGTGGACGTGACGGTACG<br>ACGAGGCGACGGCGGCACAAATAAAAACTGAACCTGGCTG | (SEQ ID NO:8) |
| V6715 | GCGTACTAGCGTACCACGTGTCGACTCTGGCATCGGTAGGGTAAG<br>GATCGGTATCGGCGGCACAAATAAAAACTGAACCTGGCTA | (SEQ ID NO:9) |
| V0652 | GCGTACTAGCGTACCACGTGTCGACTCGGTGGACGTGACGGTACG<br>ACGAGGCGACGTACTTCAAGGACAAAATACCTGTATTCCAT | (SEQ ID NO:10) |
| V0651 | GCGTACTAGCGTACCACGTGTCGACTCTGGCATCGGTAGGGTAAG<br>GATCGGTATCGTACTTCAAGGACAAAATACCTGTATTCCGC | (SEQ ID NO:11) |
| W4085 | GCGTACTAGCGTACCACGTGCAGGGGAAACCTATACTTATAAGTG<br>GAACATC | (SEQ ID NO:12) |
| R432-96 | GCGTACTAGCGTACCACGTGAGAAGTTCCAGATATTGCCTGCTT<br>(SEQ ID NO:13) | |
| V9596 | GCGTACTAGCGTACCACGTGTCGACTCGGTGGACGTGACGGTACG<br>ACGAGGCGACGACTGATCCATTAGATTCAAATGTAGGAA | (SEQ ID NO:14) |
| W1940 | GCGTACTAGCGTACCACGTGTCGACTCTGGCATCGGTAGGGTAAG<br>GATCGGTATCGACTGATCCATTAGATTCAAATGTAGAAC | (SEQ ID NO:15) |

What is claimed is:

1. A method for the detection of a diagnostic base sequence in nucleic acid in a sample, which method comprises contacting the sample under hybridizing conditions and in the presence of appropriate nucleoside triphosphates and an agent for polymerization thereof, with a diagnostic primer for the diagnostic base sequence, the diagnostic primer having a non-complementary tail sequence comprising a tag region and a detector region, such that an extension product of the diagnostic primer is synthesised when the corresponding diagnostic base sequence is present in the sample, no extension product being synthesised when the corresponding diagnostic base sequence is not present in the sample and any extension product of the diagnostic primer acts as a template for extension of a further primer which hybridizes to a locus at a distance from the diagnostic base sequence, and contacting the sample with a tag primer which selectively hybridizes to the complement of the tag region in an extension product of the further primer and is extended, and detecting the presence or absence of the diagnostic base sequence by reference to the detector region in the further primer extension product.

2. A method as claimed in claim 1 wherein a detector species is used which selectively associates with the detector region in the further primer extension product.

3. A method as claimed in claim 2 wherein the detector species emits a detectable signal when cleaved during polymerase mediated extension of the tag primer.

4. A method as claimed in claim 2 wherein the detector species emits a detectable signal upon selective association with the detector region.

5. A method as claimed in claim 4 wherein the detector species is a fluorescently labelled species and the detectable signal arises from a change in fluorescence polarisation upon selective association with the detector region.

6. A method as claimed in claim 2 wherein the detector species comprises two species each having an interactive label, which labels interact upon selective association with the detector region and release a detectable signal.

7. A method as claimed in claim 6 wherein one of the interactive labels is a chelated lanthanide and the other is a chelating group.

8. A method as claimed in claim 1 wherein the further primer extension product is captured on a solid phase using a species which selectively associates with the complement of the detector region in the further primer extension product.

9. A method as claimed in claim 1 wherein the detector species comprises a nucleotide sequence identical to the sequence of the detector region in the tail of the diagnostic primer.

10. A method as claimed claim 1 wherein the tag primer comprises a nucleotide sequence identical to the sequence of the tag region in the tail of the diagnostic primer.

11. A method as claimed in claim 1 wherein the detector region in the further primer extension product is identified by reference to its size contribution to the further primer/tag primer amplification product.

12. A method as claimed claim 1 and wherein the further primer has a non-complementary tail sequence comprising a tag region.

13. A method as claimed claim 1 and wherein the further primer is a diagnostic primer.

14. A method as claimed claim 1 wherein the melting temperature of the tag primer is higher than that of the diagnostic primer so that an increase in temperature provides a switch from diagnostic primer priming to tag primer priming.

15. A method as claimed claim 1 wherein more than one diagnostic base sequence is detected in the sample using more than one diagnostic primer, appropriate further primer (s) and tag regions.

16. A method as claimed in claim 15 wherein an identical tag sequence is used in the tail of all diagnostic primers and/or all further primers.

17. A method as claimed in claim 15 wherein an identical detector region is used in the tail of all diagnostic primers.

18. A method as claimed in claim 15 wherein one further primer is used with more than one diagnostic primer.

19. A method as claimed claim 1 wherein a terminal nucleotide of at least one diagnostic primer is complementary either to a suspected variant nucleotide or to the corresponding normal nucleotide.

20. A method for the identification of one or more variant diagnostic base sequences against a background of normal diagnostic base sequences which comprised the use of a method as claimed in claim 1.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Homo sapiens

<400> SEQUENCE: 1
gcgtactagc gtaccacgtg                                            20

<210> SEQ ID NO 2
<211> LENGTH: 30
<212> TYPE: DNA
<213> ORGANISM: Homo sapiens

<400> SEQUENCE: 2
cggtggacgt gacggtacga cgaggcgacg                                 30

<210> SEQ ID NO 3
<211> LENGTH: 30
<212> TYPE: DNA
<213> ORGANISM: Homo sapiens

<400> SEQUENCE: 3
ctggcatcgg tagggtaagg atcggtatcg                                 30

<210> SEQ ID NO 4
<211> LENGTH: 50
<212> TYPE: DNA
<213> ORGANISM: Homo sapiens

<400> SEQUENCE: 4

-continued gcgtactagc gtaccacgtg cactaatgag tgaacaaaat tctcaccatt         50

<210> SEQ ID NO 5
<211> LENGTH: 86
<212> TYPE: DNA
<213> ORGANISM: Homo sapiens

<400> SEQUENCE: 5
gcgtactagc gtaccacgtg tcgactcggt ggacgtgacg gtacgacgag gcgacggcct         60
ggcaccatta aagaaaatat catctt         86

<210> SEQ ID NO 6
<211> LENGTH: 86
<212> TYPE: DNA
<213> ORGANISM: Homo sapiens

<400> SEQUENCE: 6
gcgtactagc gtaccacgtg tcgactctgg catcggtagg gtaaggatcg gtatcggcct         60
ggcaccatta aagaaaatat cattgg         86

<210> SEQ ID NO 7
<211> LENGTH: 41
<212> TYPE: DNA
<213> ORGANISM: Homo sapiens

<400> SEQUENCE: 7
gcgtactagc gtaccacgtg atcctgaaac ccagctcaaa t         41

<210> SEQ ID NO 8
<211> LENGTH: 85
<212> TYPE: DNA
<213> ORGANISM: Homo sapiens

<400> SEQUENCE: 8
gcgtactagc gtaccacgtg tcgactcggt ggacgtgacg gtacgacgag gcgacggcgg         60
cacaaataaa aactgaacct ggctg         85

<210> SEQ ID NO 9
<211> LENGTH: 85
<212> TYPE: DNA
<213> ORGANISM: Homo sapiens

<400> SEQUENCE: 9
gcgtactagc gtaccacgtg tcgactctgg catcggtagg gtaaggatcg gtatcggcgg         60
cacaaataaa aactgaacct ggcta         85

<210> SEQ ID NO 10
<211> LENGTH: 86
<212> TYPE: DNA
<213> ORGANISM: Homo sapiens

<400> SEQUENCE: 10
gcgtactagc gtaccacgtg tcgactcggt ggacgtgacg gtacgacgag gcgacgtact         60
tcaaggacaa aatacctgta ttccat         86

<210> SEQ ID NO 11
<211> LENGTH: 86
<212> TYPE: DNA
<213> ORGANISM: Homo sapiens

<400> SEQUENCE: 11

```
gcgtactagc gtaccacgtg tcgactctgg catcggtagg gtaaggatcg gtatcgtact      60
tcaaggacaa atacctgta ttccgc                                            86

<210> SEQ ID NO 12
<211> LENGTH: 52
<212> TYPE: DNA
<213> ORGANISM: Homo sapiens

<400> SEQUENCE: 12
gcgtactagc gtaccacgtg cagggggaaac ctatacttat aagtggaaca tc             52

<210> SEQ ID NO 13
<211> LENGTH: 44
<212> TYPE: DNA
<213> ORGANISM: Homo sapiens

<400> SEQUENCE: 13
gcgtactagc gtaccacgtg agaagttcca gatattgcct gctt                       44

<210> SEQ ID NO 14
<211> LENGTH: 84
<212> TYPE: DNA
<213> ORGANISM: Homo sapiens

<400> SEQUENCE: 14
gcgtactagc gtaccacgtg tcgactcggt ggacgtgacg gtacgacgag gcgacgactg      60
atccattaga ttcaaatgta ggaa                                             84

<210> SEQ ID NO 15
<211> LENGTH: 84
<212> TYPE: DNA
<213> ORGANISM: Homo sapiens

<400> SEQUENCE: 15
gcgtactagc gtaccacgtg tcgactctgg catcggtagg gtaaggatcg gtatcgactg      60
atccattaga ttcaaatgta gaac                                             84

<210> SEQ ID NO 16
<211> LENGTH: 17
<212> TYPE: DNA
<213> ORGANISM: Homo sapiens

<400> SEQUENCE: 16
cgtaccacgt gtcgact                                                     17

<210> SEQ ID NO 17
<211> LENGTH: 18
<212> TYPE: DNA
<213> ORGANISM: Homo sapiens

<400> SEQUENCE: 17
agcaggtctg ttccaagg                                                    18

<210> SEQ ID NO 18
<211> LENGTH: 20
<212> TYPE: DNA
<213> ORGANISM: Homo sapiens

<400> SEQUENCE: 18
cttgggtgtg tagaagaagc                                                  20
```

```
<210> SEQ ID NO 19
<211> LENGTH: 26
<212> TYPE: DNA
<213> ORGANISM: Homo sapiens

<400> SEQUENCE: 19
cctgcctgtc tcccagatca ctamra                                          26

<210> SEQ ID NO 20
<211> LENGTH: 30
<212> TYPE: DNA
<213> ORGANISM: Homo sapiens

<400> SEQUENCE: 20
cactaatgag tgaacaaaat tctcaccatt                                      30

<210> SEQ ID NO 21
<211> LENGTH: 35
<212> TYPE: DNA
<213> ORGANISM: Homo sapiens

<400> SEQUENCE: 21
ctggcatcgg tagggtaagg atcggtatcg tamra                                35

<210> SEQ ID NO 22
<211> LENGTH: 37
<212> TYPE: DNA
<213> ORGANISM: Homo sapiens

<400> SEQUENCE: 22
gcgtactctg gcatcggtag ggtaaggatc ggtatcg                              37

<210> SEQ ID NO 23
<211> LENGTH: 30
<212> TYPE: DNA
<213> ORGANISM: Homo sapiens

<400> SEQUENCE: 23
gcctggcacc attaaagaaa atatcattgg                                      30

<210> SEQ ID NO 24
<211> LENGTH: 24
<212> TYPE: DNA
<213> ORGANISM: Homo sapiens

<400> SEQUENCE: 24
gcgtactcgt accacgtgtc gact                                            24
```